United States Patent
Greenhalgh

(10) Patent No.: US 7,122,052 B2
(45) Date of Patent: Oct. 17, 2006

(54) INTEGRAL SUPPORT STENT GRAFT ASSEMBLY

(75) Inventor: E. Skott Greenhalgh, Wyndmoor, PA (US)

(73) Assignee: Stout Medical Group LP, Perkasie, PA (US)

( * ) Notice: Subject to any disclaimer, the term of this patent is extended or adjusted under 35 U.S.C. 154(b) by 24 days.

(21) Appl. No.: 10/953,144

(22) Filed: Sep. 29, 2004

(65) Prior Publication Data

US 2005/0131516 A1   Jun. 16, 2005

Related U.S. Application Data

(60) Provisional application No. 60/506,897, filed on Sep. 29, 2003.

(51) Int. Cl.
   *A61F 2/06* (2006.01)
(52) U.S. Cl. ..................... 623/1.35; 623/1.13
(58) Field of Classification Search ...... 623/1.13–1.22, 623/1.35
   See application file for complete search history.

(56) References Cited

U.S. PATENT DOCUMENTS

| | | | |
|---|---|---|---|
| 5,562,724 A | 10/1996 | Vorwerk et al. ............... 623/1 |
| 5,591,228 A * | 1/1997 | Edoga ..................... 128/898 |
| 5,676,696 A | 10/1997 | Marcade ..................... 623/1 |
| 5,725,547 A * | 3/1998 | Chuter ..................... 606/194 |
| 5,824,037 A | 10/1998 | Fogarty et al. ............... 623/1 |
| 5,824,040 A * | 10/1998 | Cox et al. .................. 623/1.35 |
| 6,159,239 A | 12/2000 | Greenhalgh ................. 623/1.13 |
| 6,164,339 A | 12/2000 | Greenhalgh .................. 139/1 R |
| 6,192,944 B1 * | 2/2001 | Greenhalgh ............. 139/425 R |
| 6,193,745 B1 | 2/2001 | Fogarty et al. ............ 623/1.12 |
| 6,319,278 B1 * | 11/2001 | Quinn ....................... 623/1.13 |
| 6,325,819 B1 | 12/2001 | Pavcnik et al. ............ 623/1.11 |
| 6,352,561 B1 | 3/2002 | Leopold et al. .............. 623/123 |
| 6,428,565 B1 | 8/2002 | Wisselink .................. 623/1.11 |
| 6,524,336 B1 | 2/2003 | Papazolgou et al. ....... 623/1.35 |
| 6,551,350 B1 | 4/2003 | Thornton et al. .......... 623/1.13 |
| RE38,146 E | 6/2003 | Palmaz et al. ............. 623/1.11 |
| 6,576,009 B1 | 6/2003 | Ryan et al. ................ 623/1.35 |
| 6,592,614 B1 | 7/2003 | Lenker et al. ............. 623/1.13 |
| 6,695,875 B1 | 2/2004 | Stelter et al. .............. 623/1.13 |
| 6,773,457 B1 | 8/2004 | Ivancev et al. ............ 623/1.28 |
| 2002/0198587 A1 | 12/2002 | Greenberg et al. ......... 623/1.13 |

* cited by examiner

*Primary Examiner*—Thomas Barrett
(74) *Attorney, Agent, or Firm*—Synnestvedt & Lechner LLP

(57) ABSTRACT

A stent graft is disclosed having a tubular graft formed from flexible filamentary members interwoven with a supporting monofilament defining radial corrugations around the graft. The ends of the graft are tapered from a smaller to a larger diameter and have stents attached thereto for engagement with a vascular vessel. The stents are attached to the graft by passing through two rows of slots cut in the graft and arranged in spaced relation to one another. The slots are positioned on a reverse fold of the graft to capture the stent. The stent graft may be modular and have limbs insertable into a base module. The base module has a main central space in communication with branch central spaces defined by a line of attachment between the branch central spaces. The terminus of the line of attachment forms a shoulder for retaining the limbs.

16 Claims, 14 Drawing Sheets

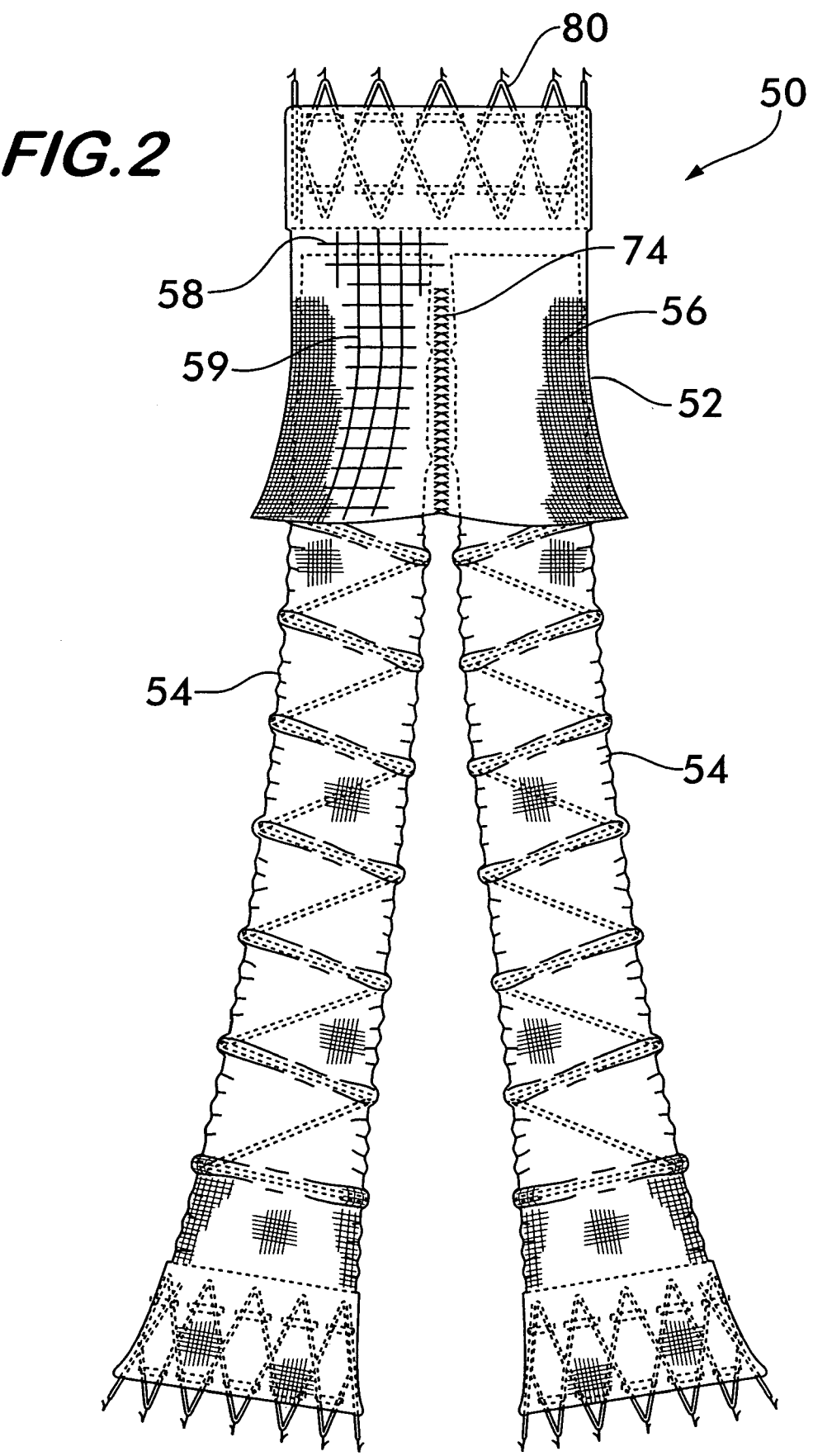

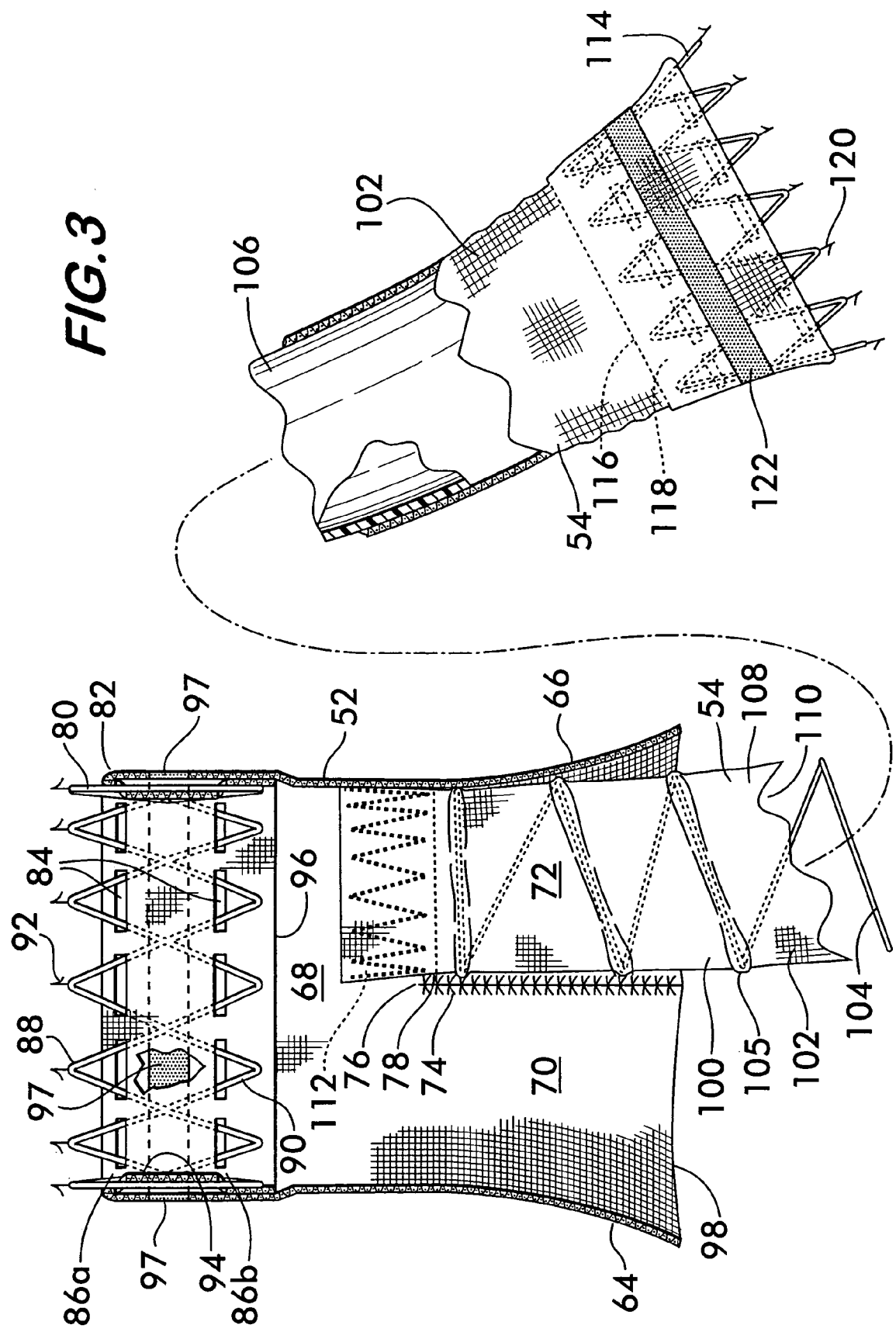

FIG. 3A
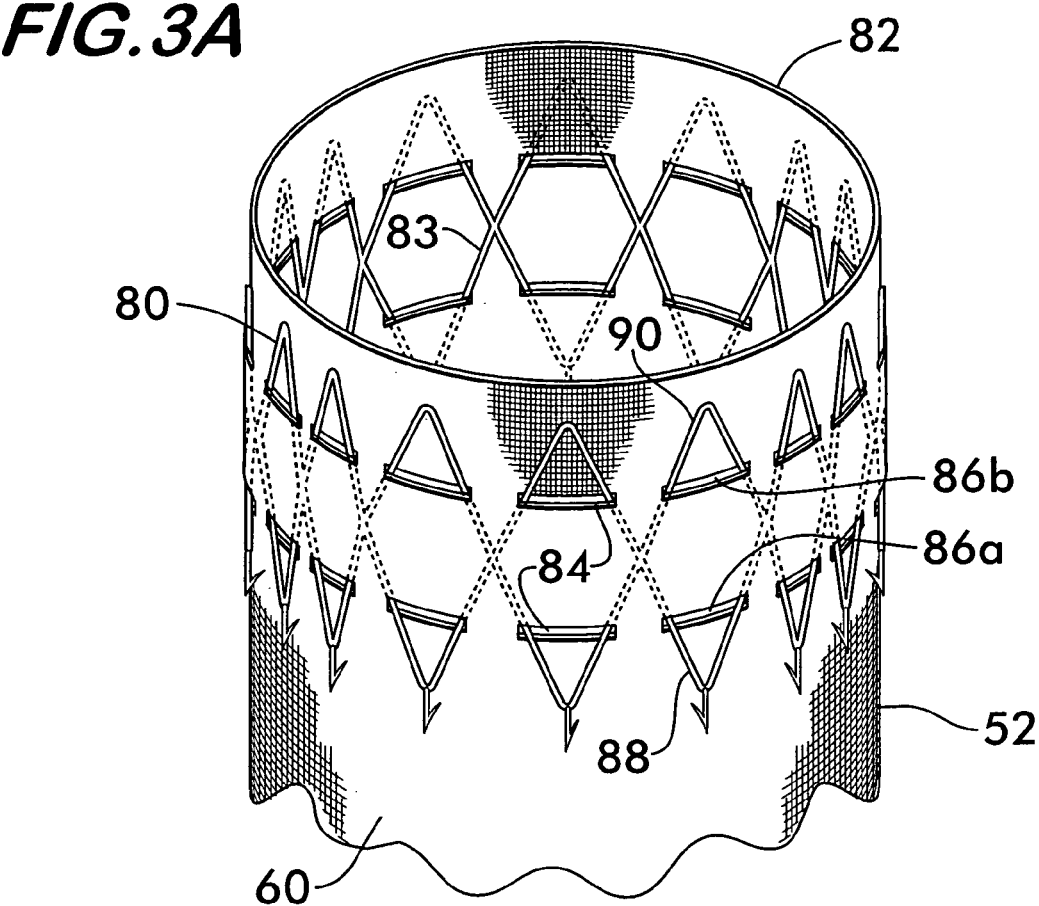
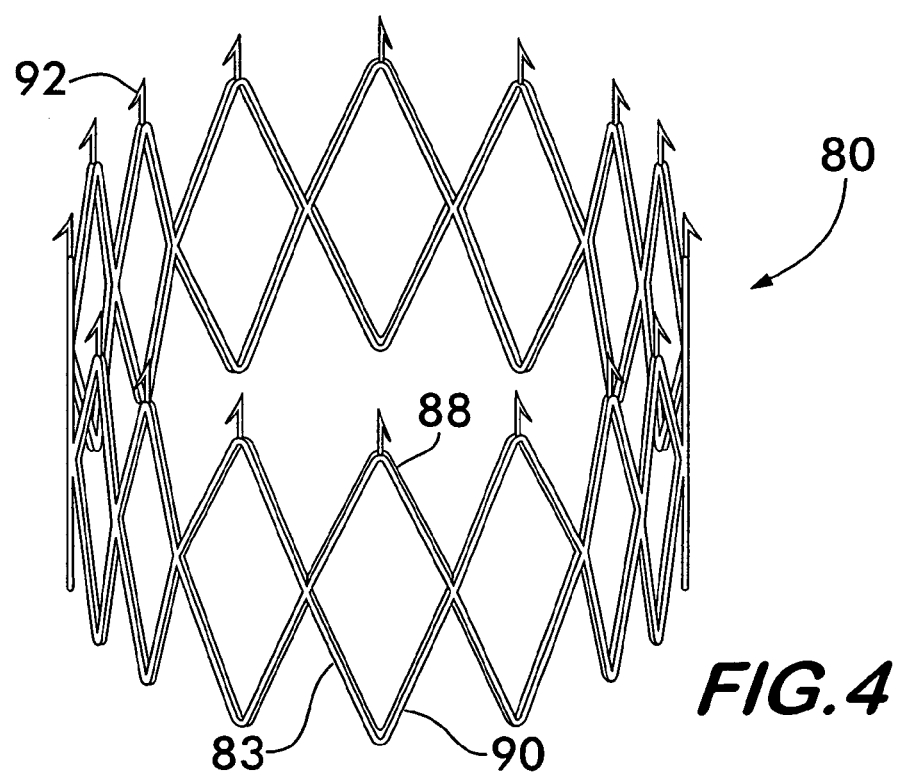
FIG. 4

INTEGRAL SUPPORT STENT GRAFT ASSEMBLY

FIELD OF THE INVENTION

This invention relates to stent grafts for treatment of vascular disorders and includes stent grafts assembled from modular components.

BACKGROUND OF THE INVENTION

The vascular system is subject to various disorders, among the more serious being occlusive diseases and aneurysms. Occlusive diseases refer to the closing of vessels such as the iliac, carotid, biliary and coronary arteries. Aneurysms are defined as a pathologic dilation of a vessel and can affect the aortic, thoracic, renal and iliac arteries among others.

Effective treatment of many occlusive diseases and aneurysms is possible through the use of an endovascular stent graft. The stent graft comprises a tubular structure (the "graft") which effects a connection between portions of a vascular vessel. The graft is typically flexible and preferably formed of biocompatible filaments or yarns interlaced by weaving, knitting or braiding to form a tube or sleeve. The stent is positioned circumferentially around and supports the graft and is preferably formed from elastic, resilient materials such as nitinol, titanium or stainless steel which have a high yield stress and are also compatible for implantation within the human body.

A particular example of the use of an endovascular stent graft to treat an aortic aneurysm is described below, it being understood that the example is for illustrative purposes only and in no way limits the invention disclosed herein to the treatment of any particular vascular disorder, as will be appreciated by those of skill in the art. It is further recognized that the invention is also applicable in the treatment of other occlusive diseases or aneurysms, such as neurological, esophageal and bronchial aneurysms.

An aneurysm, as noted above, is a pathologic dilation of a segment of a blood vessel which constitutes a weakened portion of the vessel. In a fusiform aneurysm 10, such as can occur in the abdominal aorta 12 as seen in FIG. 1, the entire circumference of the vessel is dilated and weakened. The majority of these aortic aneurysms are located in the distal abdominal aorta between the renal arteries 14 and the bifurcation point 16 where the abdominal aorta splits into the common iliac arteries 18.

Abdominal aortic aneurysms are the 13th largest cause of death in the United States. Such aortic aneurysms constitute a serious condition, as an acute rupture of the aneurysm is fatal unless an emergency operation is performed. However, even when such operations are performed in time, the mortality rate is still greater than 50%.

Modern methods of treatment for aortic aneurysms focus on providing an endovascular stent graft which is inserted within the artery at the aneurysm by means of a catheter. As seen in FIG. 1, stent graft 20 comprises a tubular graft 22, which could be woven, knitted or braided, graft 22 having one end 24 which is attached to the inner surface of the artery above the aneurysm 10. The opposite end 26 of the stent graft is split into two tubular grafts 26a and 26b which branch into and are attached to the inside surfaces of the iliac arteries 18 below the aneurysm 10. The stent graft replaces the abdominal aorta in the region of the aneurysm 10, relieving the pressure on the arterial wall and avoiding a potentially fatal rupture.

Stent graft 20 further comprises stents 28 and 30 in the form of continuous wire springs positioned in the ends 24 and 26a and 26b of the graft. Also positioned at the ends are hooks 32, arranged circumferentially around the graft with hook ends 34 facing outwardly.

The stents 28 and 30 are each formed into a plurality of crests and troughs circumferentially of the graft and normally bias the graft ends into a substantially circular, open configuration when the graft is positioned within the artery. The stents are elastically collapsible to a small diameter, however, so as to enable the graft to be advanced through the bore of a catheter which fits within the artery.

To implant the stent graft, the catheter is inserted into the aorta from one of the iliac arteries, the catheter tip being positioned within the artery above the aneurysm. The stent graft is advanced through the catheter, and when the end 24 emerges from the catheter, stent 28 expands radially outwardly under the biasing spring forces of the stent, opening the graft and filling the artery diameter. Ends 34 of hooks 32 positioned at end 24 engage and grip the inner surface of the artery, fixing the stent graft into position. The catheter is then withdrawn as the stent graft is released from the catheter. When the ends 26a and 26b emerge, the respective stents 30 expand radially within the artery, opening the stent graft 20 at ends 26a and 26b. The ends are positioned into a respective iliac artery where hooks 32 engage and grip the interior surface of the iliac arteries, thereby fixing the stent graft 20 into position within the aneurysm 10.

Use of the endovascular stent graft has proved effective at treating fusiform aneurysms, especially aortic aneurysms as described above. However, the manufacture and use of stent grafts is troublesome and expensive for several reasons.

Sutures are a Disadvantage

Normally, the stents 28 and 30 and the hooks 32 are sutured to the graft 22. Suturing is also used to attach other items, such as radiopaque markers to the graft. Suturing is necessarily a hand operation given the small size, delicacy of the components and the precision required to produce a usable stent graft. Hand suturing is done by skilled workers, and each piece takes a relatively long time to complete, resulting in low production rates and high production costs.

Furthermore, sutures can become untied during the operation or after the stent graft is implanted. If the sutures fail during the operation and the stent or hooks separate from the graft (even partially), then all of the pieces have to be retrieved and removed from the artery before another attempt to implant a stent graft can be made.

The consequences of a failure after an operation could, of course, be fatal. For example, if the end 24 of the graft separates from the stent 28 or hooks 32 due to a suture failure and the graft end 24 fails to seal within the artery or collapses into the aneurysm, the stent graft will no longer reinforce the artery, the aneurysm will be subjected to the blood pressure and acute rupture could ensue. The free graft end could also fold and partially block the artery, again with potentially fatal results.

The use of sutures also adds bulk to the stent graft. This is undesirable because it limits the minimum size of the catheter usable to implant the stent graft. The stent graft must fit within and advance along the bore of the catheter during the operation, and the bulkier the stent graft the larger a catheter is required, thereby limiting the size of artery which can be treated by the implantation of a stent graft.

Sutures also tend to snag on the walls or tip of the catheter, thus, making it difficult to smoothly advance the stent graft along the bore or readily release it from the catheter, potentially complicating the operation.

Finally, because sutures are expensive and time consuming to use, tend to increase the bulk of the stent graft and tend to snag the walls of the catheter, they are used sparingly to attach the stent and hooks to the graft. Fewer attachment points means greater potential for failure at some point during or after the operation. Clearly, there is a need for an improved stent graft wherein the stents and hooks are attached to the graft in a way which avoids the disadvantages of sutures.

Delivery and Positioning of the Stent Graft Needs Improvement

As described above, stent grafts are delivered percutaneously by means of a catheter inserted within an artery. The catheter must traverse a significant length of the artery before the catheter tip is positioned so that the stent graft may be released and expanded to attach itself to the artery wall. To accurately and easily position the catheter tip, the catheter must be flexible so as to follow the twists and turns of the artery. Stent grafts positioned within the catheter tend to stiffen it and reduce its ability to bend and easily traverse the artery for accurate positioning of the tip. The longer and more bulky the stent grafts are the more they stiffen the catheter, thereby increasing any disadvantage. Furthermore, stent grafts generally require a sheath within the catheter, thereby further increasing bulk and thus stiffness of the catheter.

Accuracy of placement is of particular importance for treatment of an aortic aneurysm, for example, so that the stent graft is attached to healthy tissue above the aneurysm but below the branch point of the renal arteries. Accurate placement insures that the stent graft will form a strong sealing attachment to healthy tissue without blocking blood flow through neighboring arterial branches.

Different Sizes of Stent Graft are Required

To effectively treat an aneurysm, the stent graft must be sized appropriately to the patient, i.e., the diameters of the attachment points must be such that they form an effective seal with the artery, and the lengths of the various branches must bridge the diseased region without being too short or having significant excess length. The diameter of the stent must match the artery so that there is smooth and substantially continuous contact between the graft and the artery wall around the circumference. Too small a stent diameter will cause one or more folds to occur in the artery, leading to an incomplete seal and leakage into the aneurysm. Too large a stent diameter will result in a fold in the graft, also causing a leak as well as an obstruction within the artery that impedes the flow of blood and which may become a point where clots form and break off to later lodge in the artery and form an embolism. If the length of a branch is insufficient, then the branch may not bridge the diseased region of the artery, placing additional stress on an already weakened artery wall. If the lengths are too great, then the branches may kink and impede blood flow.

Assurance that the proper size stent graft is available requires either that each stent graft be custom made for each patient, or that a large number of stent grafts covering a broad spectrum of sizes be available. The impracticality of both solutions leads to significant expense in the treatment of vascular disorders.

Clearly, there is a need for improved stent grafts for the treatment of vascular disorders.

SUMMARY OF THE INVENTION

The invention concerns a stent graft for repair of a vascular vessel. The stent graft comprises a graft formed of a plurality of flexible filamentary members interwoven to form an elongated tube. A stiffening monofilament is interwoven with the flexible filamentary members. The monofilament extends helically around the tube and forms a reinforcing rib integral with the tube thereby defining a plurality of circumferential corrugations in the tube. A stent is positioned at one end of the tube. The stent surrounds the one end and is deformable between a collapsed configuration and an expanded configuration. In the expanded configuration the stent supports the tube in an open configuration. The one end is tapered from a smaller to a larger diameter for providing sealing engagement with the vascular vessel.

In one embodiment, the first tube segment comprises a first sidewall portion defining a first central space and second and third sidewall portions defining second and third central spaces. The second and third central spaces are in fluid communication with the first central space. A line of attachment is formed between the second and third central spaces by joining opposing portions of the sidewall portions together. The line of attachment has a terminal point positioned at a junction of the first, second and third central spaces and thereby forms a shoulder within the graft. An end of the one branch segment has a stent attached to it and is insertable within, for example, the second central space. The end having the stent is engageable with the shoulder, and engagement between the end and the shoulder retains the one branch segment to the first tube segment.

The stent according to the invention may further comprise a second branch segment having a second stent positioned at one end thereof. The one end of the second branch segment is insertable within the third central space and is also engageable with the shoulder. Engagement between the second branch segment and the shoulder retains the second branch segment to the first tube segment.

Preferably, the first branch segment has a second stent positioned at an opposite end thereof. The second stent surrounds the opposite end of the second stent, the opposite end being tapered from a smaller to a larger diameter for providing sealing engagement with the vascular vessel.

Stents used in the invention may comprise a plurality of first projections extending in a first direction and a plurality of second projections extending in a second direction opposite to the first projections. The end of the tube to which the stent is attached comprises a reverse fold having a plurality of first openings in the tube in a first row extending circumferentially around the reverse fold, and a plurality of second openings in the tube in a second row extending circumferentially around the reverse fold. The first and second rows of openings are positioned in spaced relation to one another, the stent being positioned between the first and second rows. The first projections extend through the first openings in the first row and the second projections extending in an opposite direction through the second openings in the second row, the stent being thereby retained to the graft.

It is advantageous to provide a region of enhanced biocompatibility positioned on the tube of the stent adjacent to the reverse fold. The region of enhanced biocompatibility faces radially outwardly and facilitates the formation of a biological seal between the stent graft and the vascular vessel.

In another embodiment of the invention concerning a bifurcated stent graft for repair of a bifurcated vascular vessel, the stent graft comprises a first elongated tubular segment having a stent for supporting the segment in an open configuration at one end. First and second branch tubular segments extend from an opposite end of the first elongated tubular segment and are in fluid communication with it. The branch tubular segments each have a free end distal to the first elongated tubular segment. Respective stents are positioned at the free ends for supporting them in an open configuration. The first and second branch tubular segments are lengthwise collapsible so as to fit within the first elongated tubular segment. The first and second branch segments are extendible lengthwise from the first elongated tubular segment for sealing engagement with the bifurcated vascular vessel.

BRIEF DESCRIPTION OF THE DRAWINGS

FIG. 2 is a side view of an integral support stent graft assembly according to the invention;

FIG. 3 is a longitudinal sectional view of a partially assembled integral support stent graft assembly;

FIG. 3A is a perspective view of a portion of the integral support stent graft of FIG. 3;

FIG. 4 is a perspective view of a stent used with the integral support stent graft assembly shown in FIG. 3;

DETAILED DESCRIPTION OF THE PREFERRED EMBODIMENTS

Figure 1:
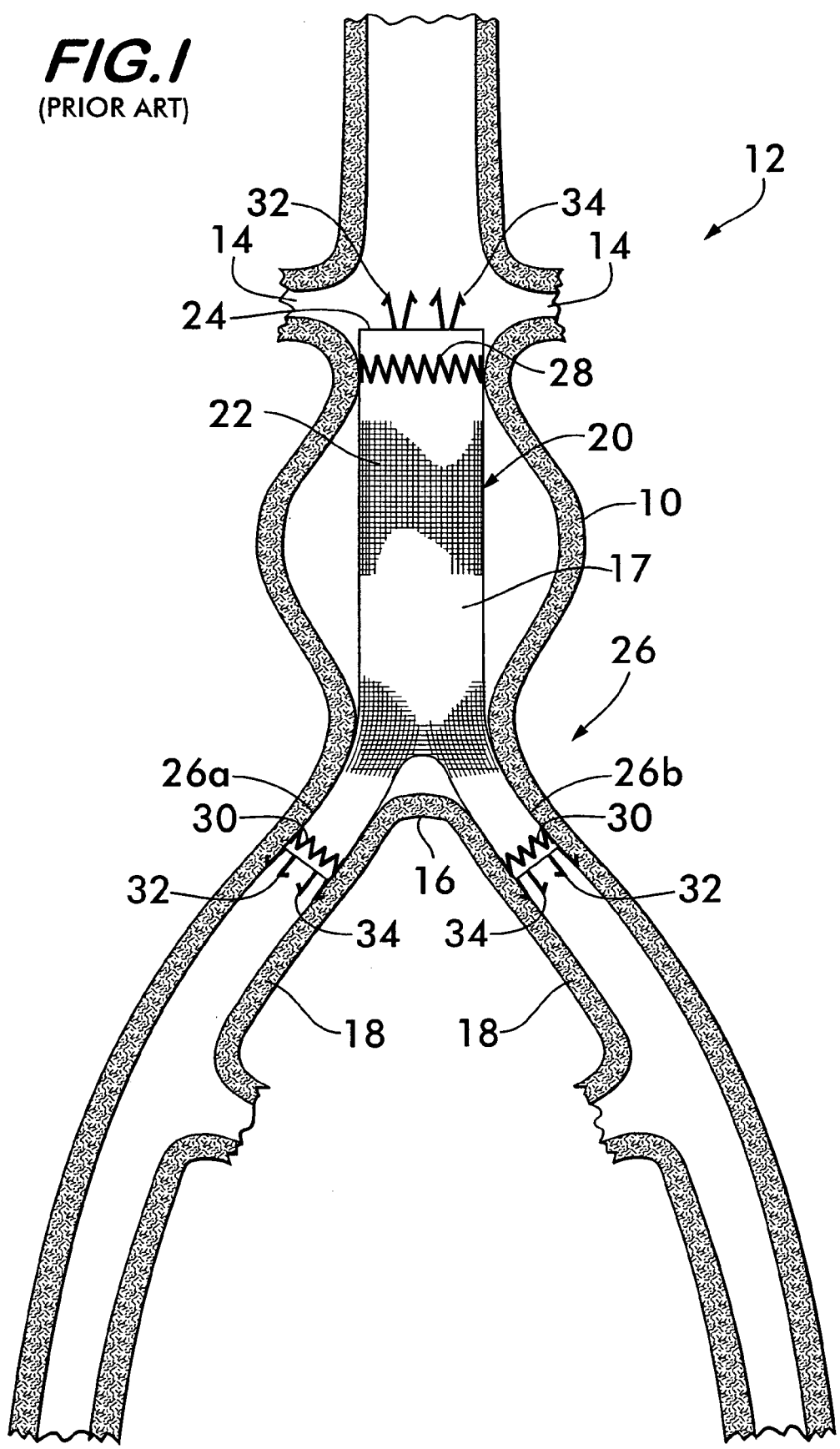
FIG. 1 is a longitudinal sectional view of an abdominal aortic aneurysm treated using a stent graft according to the prior art.

FIG. 2 shows a integral support stent graft assembly 50 according to the invention. Assembly 50 comprises a base module 52 to which a plurality of limbs 54 may be attached upon assembly to form a stent graft for repair of an aneurysm, such as an aortic aneurysm as described below.

Base module 52 is preferably formed of a flexible woven fabric of interlaced filamentary members 56, preferably polyester yarns, that may be multi-filaments or monofilaments. Polyester is preferred for its compatibility with living tissue, high strength, toughness, abrasion resistance and long history of success in surgical implants. Other biocompatible materials are also feasible, including polypropylene, nylon, polytetrafluoroethylene, as well as other polymers. Non-woven membranes may also be used to form base module 52, the membranes being formed of expanded polytetrafluoroethylene for example.

Filamentary members 56 are woven in a dense weave having low porosity so as to be substantially fluid tight and prevent leakage of blood into the aneurysm being repaired. Ripstop filaments 58, having higher tensile strength than the surrounding filamentary members 56, are interwoven with them to reinforce the base module 52. High strength filaments 59 are also interwoven longitudinally (preferably the warp direction) for further strength reinforcement. The filaments 59 may have a larger diameter than the surrounding filamentary members so as to provide additional wear resistance.

Figure 9:
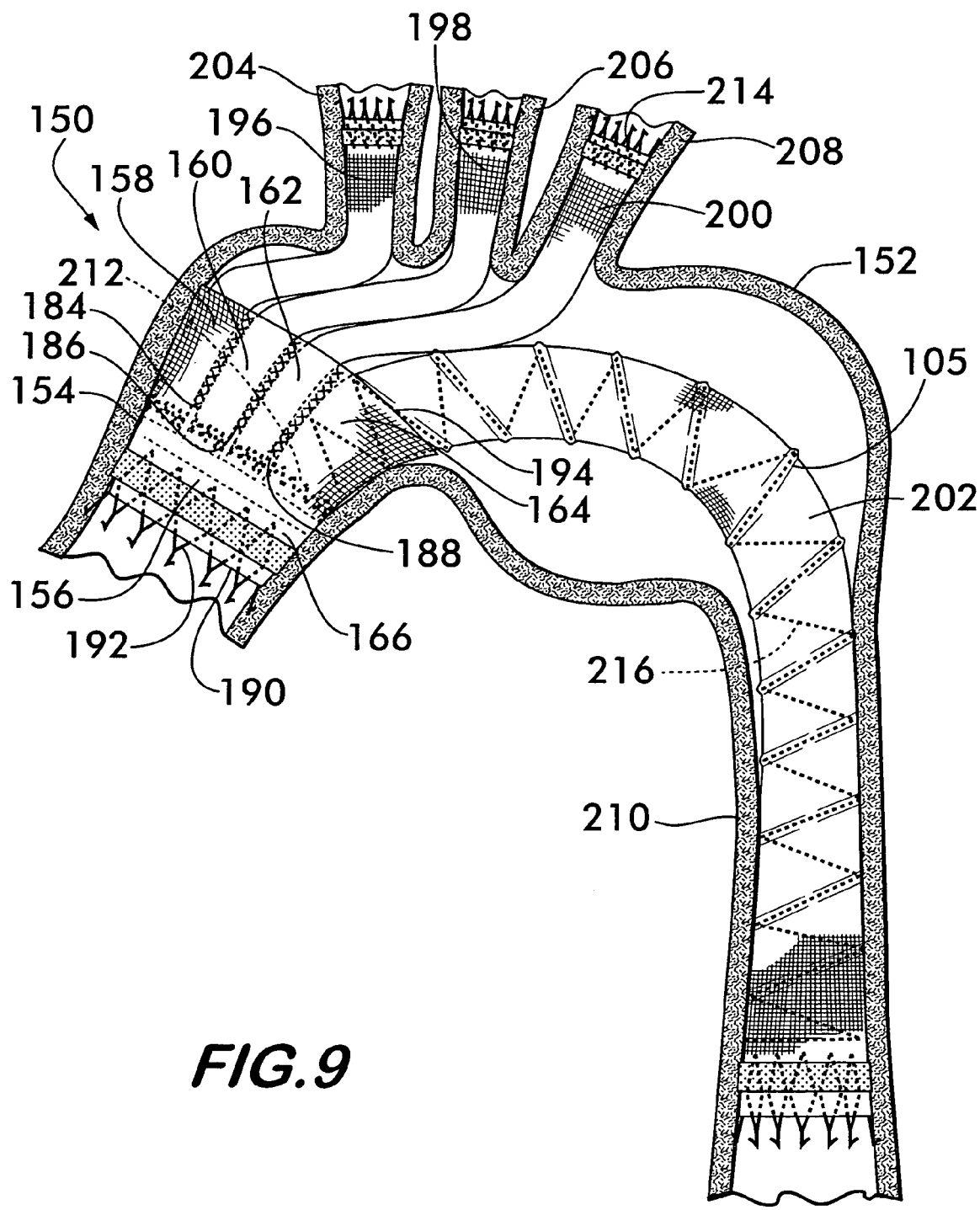
FIG. 9 is a longitudinal sectional view of an integral support stent graft assembly used to treat a descending aortic aneurysm.

As shown in longitudinal cross-section in FIG. 3, the base module 52 has a perimetral sidewall 60 that is divided into a main sidewall portion 62 and branch sidewall portions 64 and 66. Main sidewall portion 62 surrounds and defines a main central space 68 and branch sidewall portions 64 and 66 surround and define branch central spaces 70 and 72, respectively. Branch central spaces 70 and 72 are in fluid communication with the main central space 68. The branch sidewall portions 64 and 66 (and others, if present) are formed by attaching opposing portions of the perimetral sidewall 60 together along a line of attachment 74 extending lengthwise along the base module 52. For woven grafts, this is preferably done by weaving the opposing portions of the perimetral sidewall 60 together as it is being formed. It also could be accomplished by sewing the opposing portions to one another, adhesive bonding, heat fusing, as well as other techniques. Although shown having substantially the same diameter, the branch sidewall portions 64 and 66 may have different diameters simply by shifting the location of the line of attachment 74. Three or more branch central spaces may be defined by using multiple lines of attachment in spaced relation to one another, as shown in FIG. 9.

Line of attachment 74 has a terminal point 76 located at the junction of the main central space 68 and the branch central spaces 70 and 72. Terminal point 76 forms a shoulder 78 between the branch central spaces. The shoulder 78 provides a bearing surface for securing the limbs 54 to the base module 52 as described in detail below.

A stent 80 is attached to base module 52, preferably at a distal end 82 of the main sidewall portion 62. Stent 80 is compatible with living tissue and may comprise a resilient flexible material with a high yield stress. Shape memory metals such as nitinol and elgiloy are advantageous, as well as metals such as stainless steel or titanium. Engineering plastics are also feasible. As shown in FIG. 4, stent 80 preferably comprises a plurality of interconnected loops 83 which extend circumferentially to form a ring structure that supports the perimetral sidewall 60 in an expanded configuration (shown in FIG. 3) but which is also deformable into a collapsed state that will allow it to pass through a catheter. The stent 80 may be self-expanding, i.e., resiliently biased to assume the expanded configuration in the absence of restraining forces, as when released from a catheter, or it may be yieldably expandable from the collapsed state using an inflatable balloon.

FIG. 3 illustrates how the stent 80 is attached to the base module 52. The base module 52 has a plurality of openings, preferably in the form of slots 84 which extend around the main sidewall portion in two substantially parallel rows 86a and 86b, the rows being positioned in spaced relation to one another. Slots 84 are preferably formed by laser cutting the perimetral sidewall 60, laser cutting being advantageous because it fuses the cut ends of the filamentary members 56 together to prevent fraying.

The slots 84 are spaced circumferentially around the base module to align with the loops 83 of the stent 80. Each loop 83 has opposite ends 88 and 90 which project in opposite directions along the lengthwise direction of the base module 52. Each end extends through a respective slot 84 with which it aligns. Ends 88 extend through slots 84 in row 86*a*, and ends 90 extend in the opposite direction through slots 84 in row 86*b*. Ends 88 may have a hook 92 extending outwardly to anchor the stent 80 to living tissue of an artery wall. Ends 90 are preferably rounded so as not to puncture or abraid the perimetral sidewall 60.

FIG. 3A illustrates a preferred way of attaching stent 80 to a graft, for example, the distal end 82 of the base module 52. Slot rows 86*a* and 86*b* are formed in the sidewall 60 as described above, the slots of row 86*b* being between the distal end 82 of the base module 52 and the slots of row 86*a*. The stent 80 is inverted relative to the base module 52 and positioned between the rows of slots 86*a* and 86*b*. The loops 88 of the stent are inserted through the slots in row 86*a*. Loops 90 are then inserted through slots in row 86*b* and the distal end 82, along with the stent 80, is turned inside out to form a reverse fold 94 in the sidewall 60 as shown in FIG. 3. Reverse fold 94 acts to capture and retain the stent 80.

Preferably, the sidewall region 96 comprising the reverse fold 94 and the portion of the graft which it overlaps is half the thickness of the sidewall comprising the main and branch sidewall portions 62, 64 and 66. The reduction in sidewall thickness is designed to reduce the bulk of the base module 52 so that it does not adversely affect the stiffness of the catheter through which it is delivered as explained below. The reverse fold 94 also increases the abrasion resistance of the distal end 82 by providing two overlying layers through which an item, such as the stent 80, will have to abraid before becoming a problem. If necessary, the distal end 82 may be reinforced by interweaving additional high strength filamentary members, or the entire distal end could be made of the high strength fibers to ensure that the fabric holding the stent 80 does not fail under tensile forces between the stent and the graft.

It is advantageous to provide a region 97 at or adjacent to distal end 82 of main sidewall portion 62 which encourages the development of a biological seal between the living tissue of an artery and the base module 52. A biological seal is formed when cells grow in and around the textured surface of the fabric or membrane forming the sidewall, the textured surface facilitating adhesion and healing. This is encouraged by using material, such as interwoven polypropylene filaments, which causes an aggressive healing reaction in living tissue. It may also be accomplished by providing interstices in the sidewall, either by controlling the density of the weave over a particular region of the sidewall or by cutting openings in the sidewall which have a size that favors cell growth. Additionally, the sidewall may be coated with compounds such as thrombin and collagen which also cause cells to attach and grow into the sidewall. By confining these coatings, special materials and interstices to the outside of the base module 52 through the use of the reverse fold 94, the blood flow through the main central space will not be adversely affected by clotting, as might otherwise occur if coatings or interstices were also on the inner surface of the main sidewall portion 62.

The proximal end 98 of the base module 52 is flared to facilitate insertion of limbs 54 into the branch central spaces 70 and 72. Limb 54 preferably comprises an elongated outer sheath 100 of interlaced, flexible filamentary members 102 formed from a polymer such as polyester for the same reasons as provided above for the base module 52. Other polymers are also feasible. Interlacing of filamentary members 102 is preferably by weaving to provide radial stiffness to keep the limb 54 open and avoid kinking when bending, as may occur when a subject in which the limb is implanted moves. Radial stiffness to ensure patency of limbs 54 also allows a longer length of limb to be used without fear of the limb kinking. This will allow greater freedom of movement of the limbs 54 relatively to the base module 52, both lengthwise as well as angularly. The freedom of movement allows the stent graft assembly 50 to compensate for variations in size of the affected arteries over time as well as variations caused by patient motion. If a longer limb is needed, the limb 54 extends to follow a straighter path; if a shorter limb is required, the limb 54 will bend and follow a more tortuous path but will not kink and impede blood flow.

The radial stiffness of the graft may be augmented by interlacing a stiffening monofilament 104 with the polyester members 102. Stiffening monofilaments 104 are preferably interwoven with members 102 and extend helically around the sheath 100. The stiffening monofilaments 104 may be formed of nitinol, elgiloy, stainless steel or titanium or from engineering plastics for compatibility with living tissue. The stiffening monofilaments are biased to provide a radially outward force on the sheath 100 and define a plurality of circumferential corrugations 105. The corrugations provide radial stiffness to the graft while allowing the graft to remain flexible so as to allow limb 54 to collapse and pass through a catheter. If necessary, a liner 106 is positioned within sheath 100 to provide a fluid tight lining preventing leaks from limb 54. Liner 106 may be formed from interlaced filamentary members (preferably polyester) and is preferably woven to limit porosity. Sheath 100 along with liner 106, when present, form another perimetral wall 108 surrounding a central space 110, the central space being in fluid communication with either of the branch central spaces 70 and 72 and the main central space 68.

Stents 112 and 114, which may be similar to stent 80, are positioned at each end of the limb 54 and are attached thereto by the use of slots 116 and reverse folds 118 as described above for the base module 52. Stent 112, at the distal end of limb 54, attaches the limb to the base module 52 by engaging the shoulder 78 upon expanding within the branch central space 70 or 72. Expansion may be effected by use of a balloon or by resilient biasing of the stent 112 into the expanded configuration and allowing it to expand upon release from a catheter as described below. Preferably, stent 112 has no hooks which might penetrate the branch sidewall portion 64 or 66 and instead relies on friction and bearing against the shoulder 78 to remain attached to the base module 52. The stent 112 is positioned above the shoulder 78 so that, upon expansion, the stent 112 and the limb 54 are larger in diameter than the branch central space 72 in which the limb is inserted. Expansion of the stent 112 to this larger diameter causes the limb 54 to be captured by the shoulder 78 within the branch central space 72.

Stent 114, at the proximal end of limb 54, attaches to arterial tissue, for example, the iliac artery, by the use of outwardly extending hooks 120. As for the base module 54, the proximal end of limb 54 around stent 114 may have a biocompatible region 122 formed by special materials provoking a healing response, by interstices or openings having a particular size, by a textured surface and by the use of coatings such as collagen and thrombin. Preferably, the proximal end of limb 54 is tapered from a smaller to a larger diameter. The taper improves the contact and sealing between the end of limb 54 and the vascular vessel with which it is used. By tapering only the region of the limb near the proximate end, the overall bulk of the graft is reduced. This is advantageous for catheter delivery, a less bulky graft fitting within a smaller catheter and having less adverse effect on the catheter stiffness.

Figure 5:
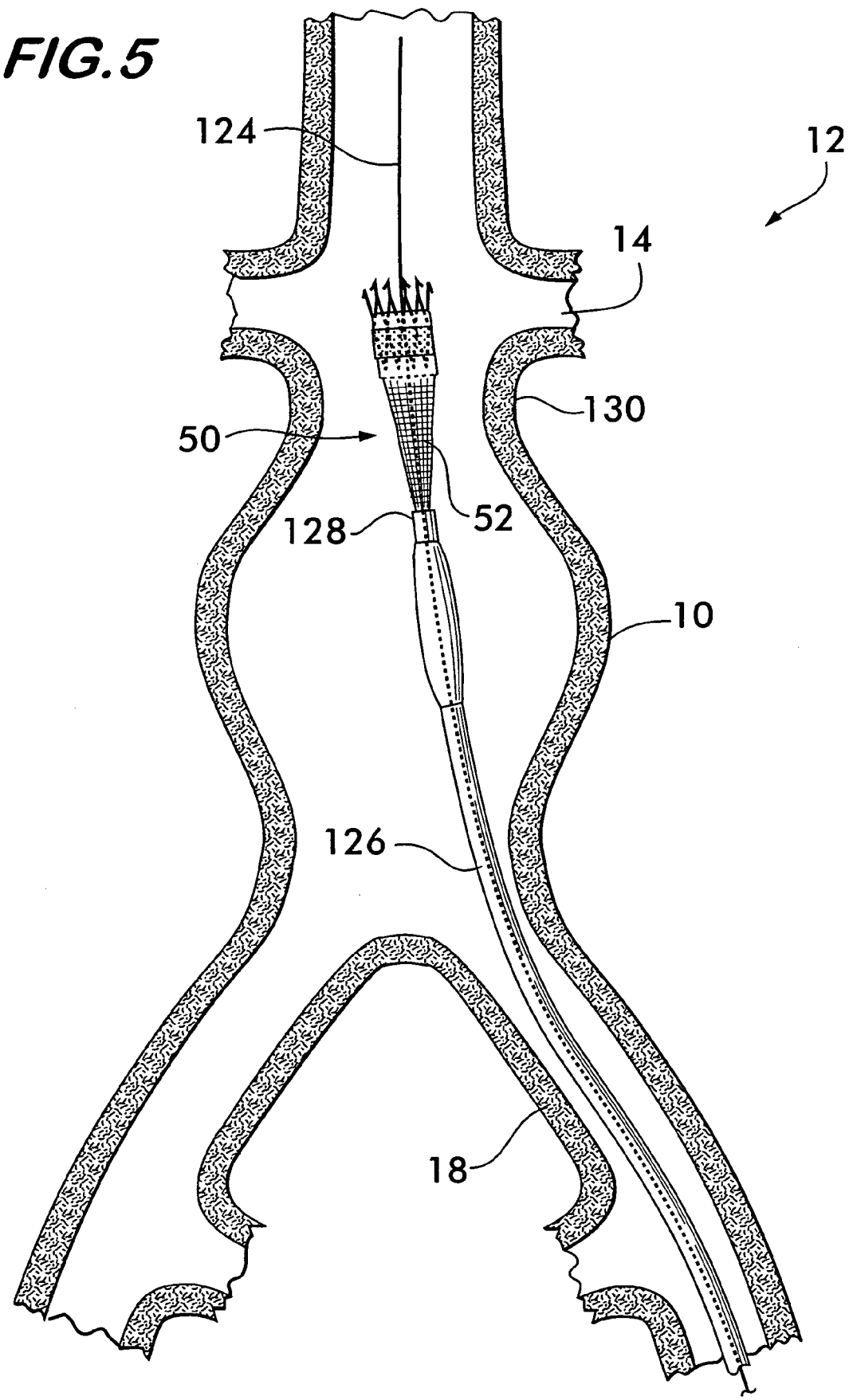
FIGS. 5–8 are longitudinal sectional views depicting steps in the treatment of an aortic aneurysm using the integral support stent graft assembly according to the invention.
Figure 6:
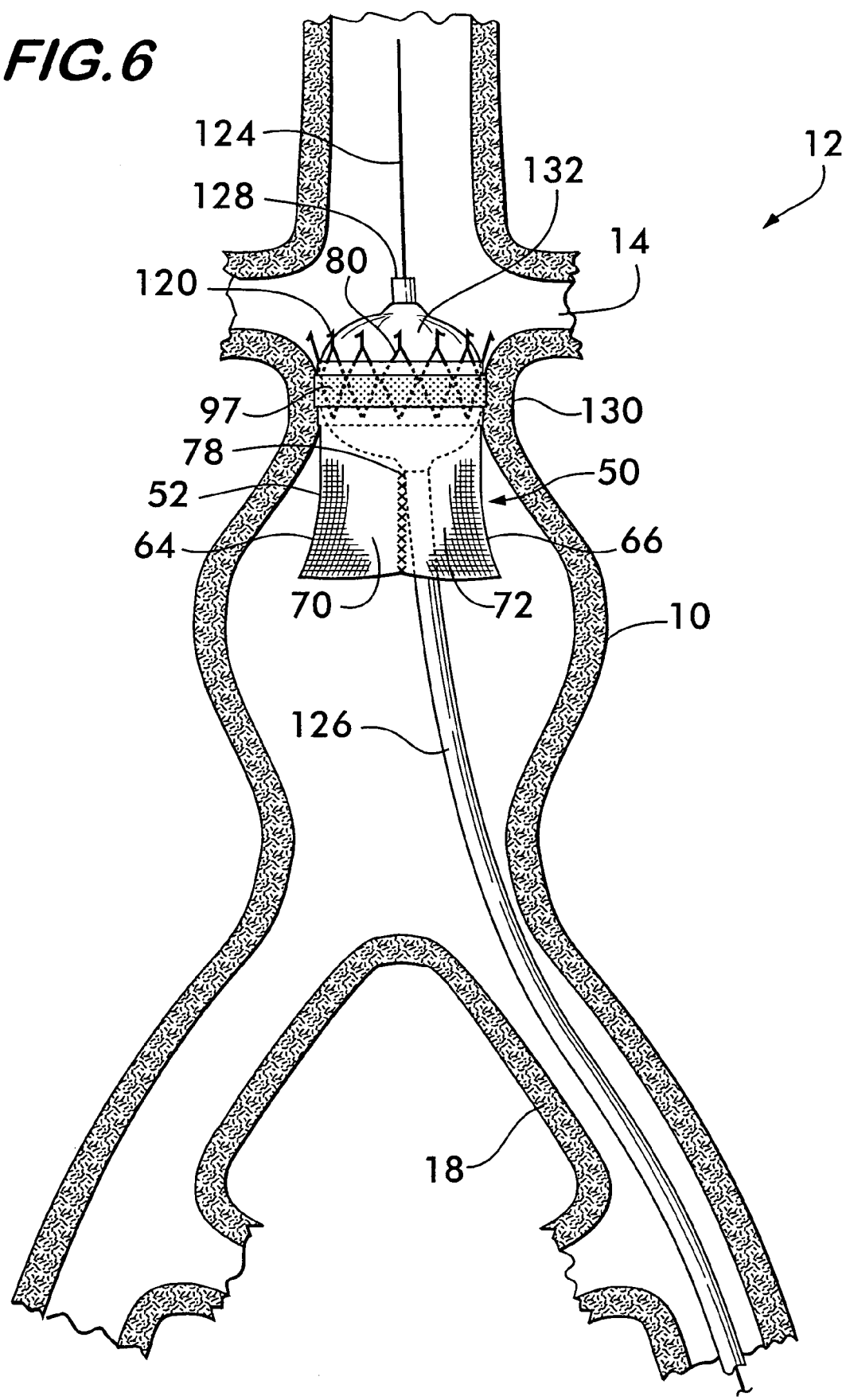

Insertion of the integral support stent graft assembly 50 in the abdominal aorta 12 to treat an aortic aneurysm 10 is illustrated in FIGS. 5–8. As shown in FIG. 5, a guide wire 124 is used to guide a catheter 126 through the abdominal aorta 12 to position the catheter tip 128 at a region of healthy tissue 130 between the renal arteries 14 and the aneurysm 10. As shown in FIG. 6, the base module 52 is forced out from the catheter tip 128 and then expanded so that the hooks 120 on stent 80 engage the aorta 12, preferably just above region 130 to initially anchor the base module 52 to the aorta. Accuracy of placement is important so that the healthy tissue is engaged by hooks 120 (and not the weakened tissue of the aneurysm 10) and also to ensure that the renal arteries 14 are not blocked by the base module 52. Greater placement accuracy as compared with prior art stent grafts (FIG. 1, for example) is afforded by the relatively short length of the base module 52, which also is more flexible when positioned within the catheter and tends, therefore, not to adversely stiffen it to make traversal of the artery difficult.

Expansion of the stent 80 may be by a balloon 132 as illustrated, but the stent may also be resiliently self expanding by itself upon release from catheter 126. Expansion of the base module 52 also brings the bioactive region 97 into contact with the healthy living tissue region 130 so as to allow eventual formation of a biological seal between the base module 52 and the aorta 12.

Figure 7:
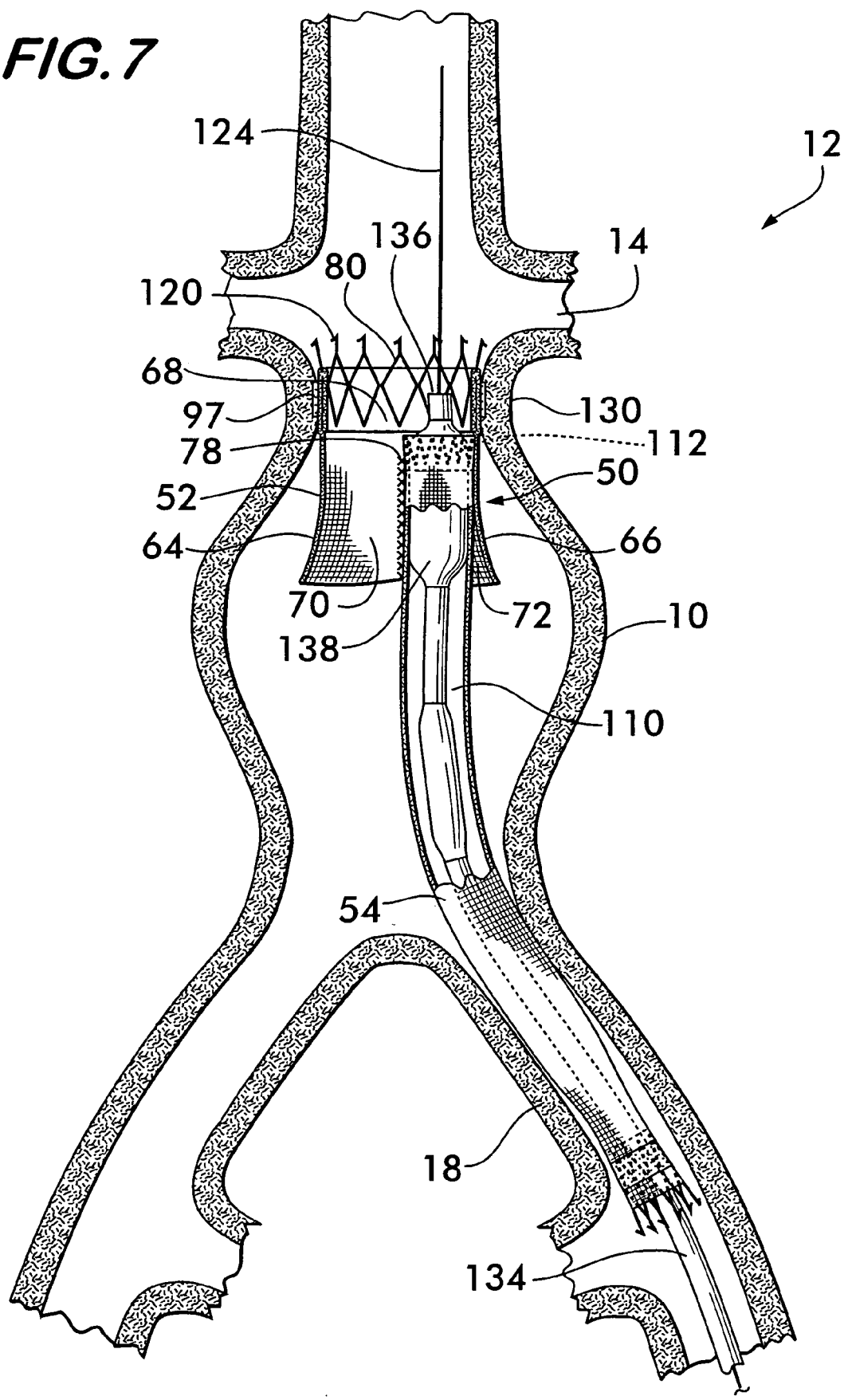

As shown in FIG. 7, catheter 126 is withdrawn and another catheter 134 traverses the abdominal aorta 12 using guide wire 124 to position its tip 136 within branch central space 72. The limb 54 is positioned within catheter 134 and is released with its distal end adjacent to shoulder 78. The stent 112 on the distal end of limb 54 is expanded, for example, by balloon 138, and the stent 112 engages the shoulder 78 to lock the limb 54 within the branch central space 72. The main central space 68, the branch central space 72 and the central space 110 of limb 54 are all in fluid communication with one another and provide a conduit which bridges the aneurysm 10, thereby relieving pressure on it to reduce its chance of rupture.

Figure 8:
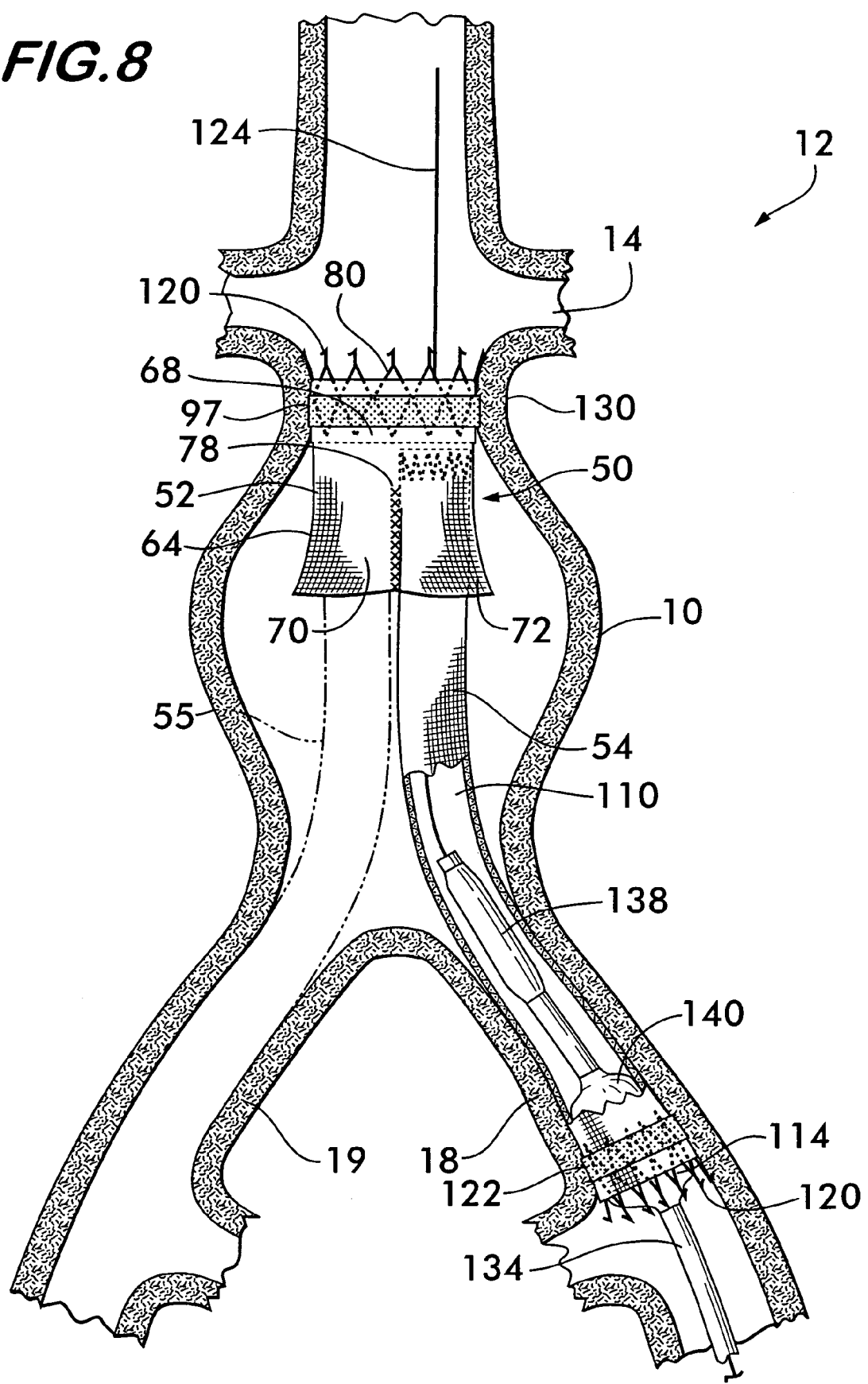

As shown in FIG. 8, the remainder of limb 54 is released from catheter 134 and the proximal end with stent 114 is positioned within an iliac artery branch 18. Stent 114 is expanded by a second balloon 140 so that its hooks 120 engage the iliac artery 18 and initially anchor the limb in place, the tapered aspect of the limb facilitating limb and artery engagement. The bioactive region 122 engages the iliac artery 18 to promote the formation of a biological seal between the limb 54 and the artery. It is preferred to have two different size balloons 138 and 140 in the catheter 134 to ensure that each stent 112 and 114 is expanded to the proper size, matched, for stent 112, to the diameter of the branch central space 72, and for the stent 114, to the diameter of the iliac artery branch 18. Dual balloons on the same catheter also eliminate the need for a catheter exchange, thereby decreasing the potential for trauma to the patient.

Catheter 134 remains flexible because only one limb 54 is within it. This is unlike prior art stent grafts 20, such as shown in FIG. 1, in which the entire stent graft is within the catheter. The other limb 55 of the integral support stent graft assembly, shown in dotted line, is connected to the other branch central space 70 as described above, but using a second catheter. Access to the aneurysm site is provided through the other branch of the iliac artery 19.

Figure 10:
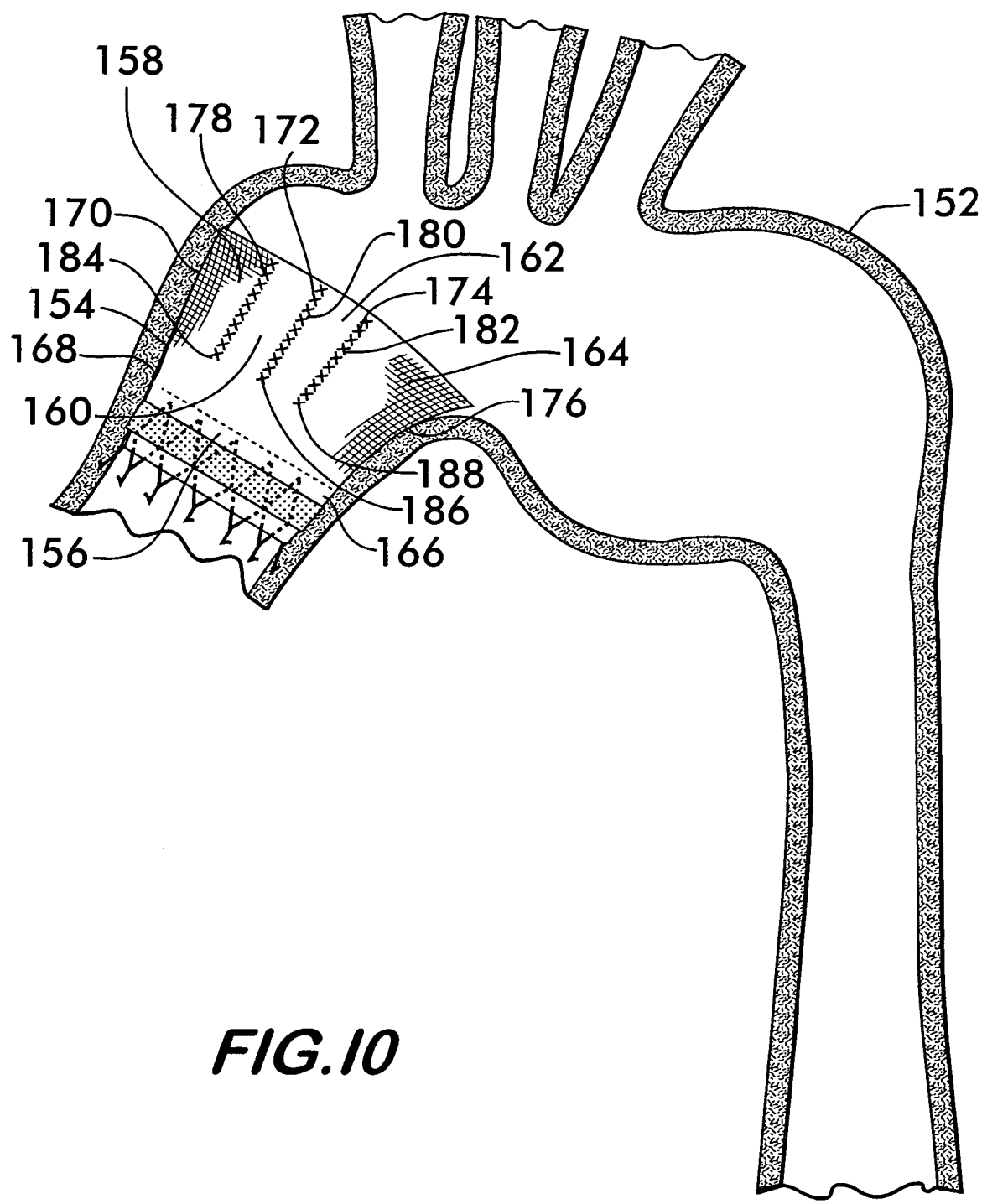
FIG. 10 is a longitudinal sectional view of a detail of a component shown in FIG. 9.

FIG. 9 illustrates the use of a integral support stent graft assembly embodiment 150 according to the invention to treat a descending aortic aneurysm 152. As shown in detail in FIG. 10, stent graft assembly 150 comprises a base module 154 having a main central space 156 and four branch central spaces 158, 160, 162 and 164 in fluid communication with the main central space. The central spaces are defined by a perimetral sidewall 166 comprising a main sidewall portion 168 and various branch sidewall portions 170, 172, 174 and 176. As described above, the central spaces are formed by attaching opposing portions of the perimetral sidewall 166 to one another along lines of attachment 178, 180 and 182, each line of attachment having a terminal point forming a respective shoulder 184, 186 and 188.

As shown in FIG. 9, the distal end 190 of base module 154 has a stent 192 for attachment to healthy aortic tissue. The proximal end 194 is flared to receive limbs 196, 198, 200 and 202. Limbs 196, 198 and 200 are sized to connect branch central spaces 158, 160 and 162 to the left subclavian artery 204, the left common carotid artery 206 and the brachiocephalic trunk 208 respectively. Limb 202 connects branch central space 164 to healthy tissue of the descending aorta 210 bridging the aneurysm 152. As described above, each limb has a hookless stent 212 at its distal end which engages shoulders 184, 186 and 188. The proximal ends of the branches have hooked stents 214 to fix those ends to tissue. Both the base module 154 and the limbs 196, 198, 200 and 202 may have zones facilitating the formation of biological seals as described above. Again, the proximal ends of the limbs are preferably tapered to facilitate limb and arterial engagement.

As described above, all of the limbs are designed to have radial stiffness. To further ensure limb patency, the radial stiffness is augmented by interweaving stiffening monofilaments 216 with filamentary members forming the limb. Multiple stiffening monofilaments 216 may be positioned in the fill direction during weaving by stopping the forward loom motion and moving a shuttle carrying the monofilament through the shed multiple times to create multiple loops of monofilament at one section. Once the monofilament is laid in, the forward motion of the loom is restarted and polymer fill yarns are woven with the warp yarns. When the position of the next monofilament is reached, the loom forward motion is again stopped and multiple passes of the monofilament carrying shuttle through the shed are effected. By repeating this pattern, a circumferentially corrugated limb will be formed, the corrugations 105 allowing excellent bending flexibility but significant radial stiffness.

Figure 11:
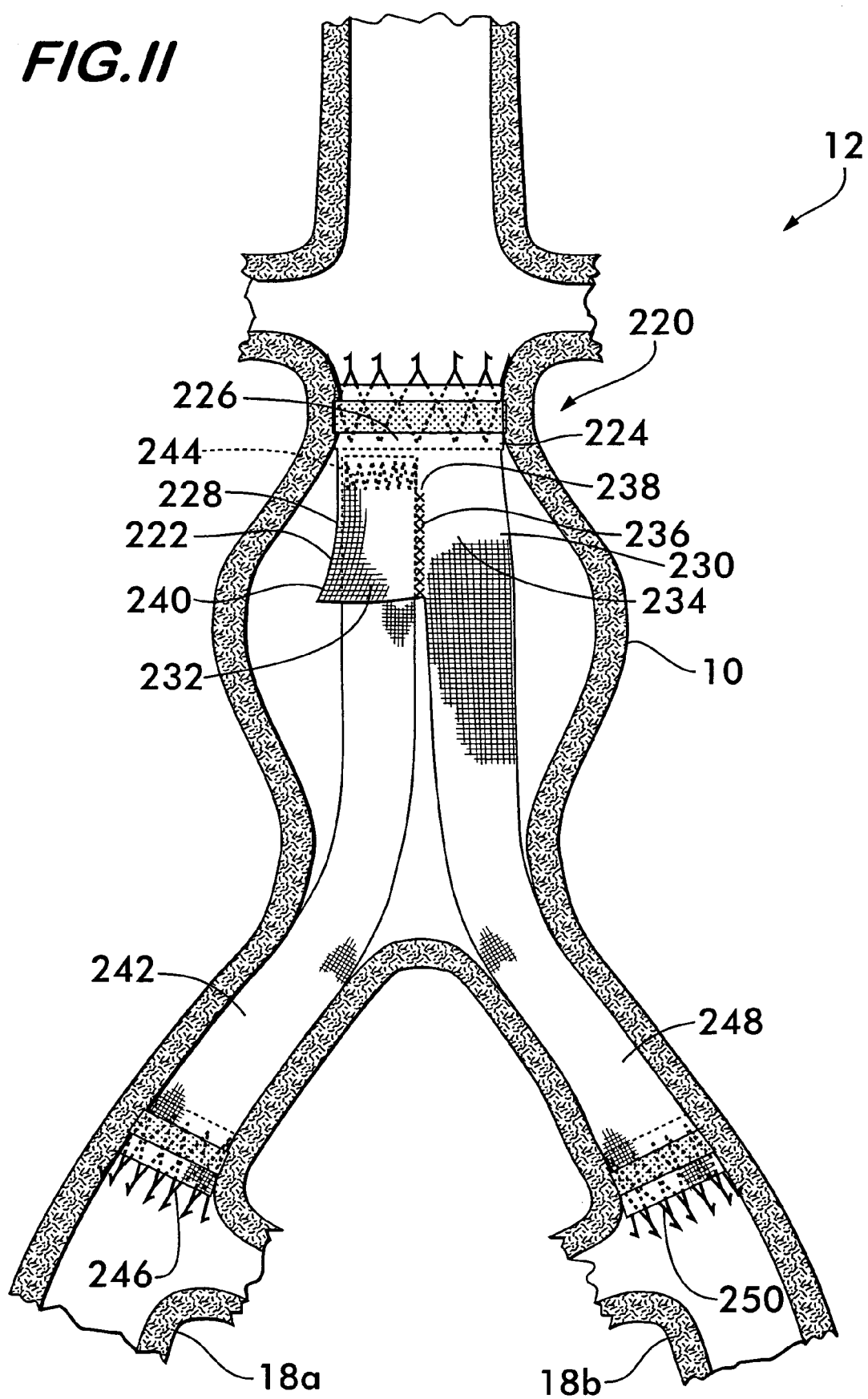
FIG. 11 is a longitudinal sectional view of another embodiment of an integral support stent graft assembly according to the invention.

FIG. 11 depicts another embodiment 220 of the integral support stent graft assembly according to the invention which may be used to treat an aneurysm 10 within the abdominal aorta 12. Stent graft 220 comprises a base module 222 having a main sidewall portion 224 defining a main central space 226. Two branch sidewall portions 228 and 230 extend from the base module 222 and each defines a respective branch central space 232 and 234 in fluid communication with the main central space 226. A line of attachment 236 divides the branch central spaces 232 and 234 and forms a shoulder 238 between the branch and central sidewall portions. Branch sidewall portion 228 is open at its flared proximal end 240 to receive a limb 242 having stents 244 and 246 at either end respectively. Stent 244 engages the shoulder 238 to lock the limb 242 into fluid communication with the main central space 226, and stent 246 attaches the other end of the limb 242 to an artery, such as a branch of the iliac artery 18a. Branch sidewall portion 230 is integrally formed with a limb 248 which has a stent 250 at it proximal end for facilitating attachment to an artery, such as the iliac artery branch 18b. Integral support stent graft assembly 220 provides the advantage of fewer separate components and fewer joints, thus reducing the potential for failure of the stent graft. Having a single separate limb 242 allows the graft to be conveniently implanted in two steps using catheters in each iliac artery branch 18a and 18b. First, the base module 222 is implanted using a catheter passing through the iliac artery branch 18b. The integrally attached limb 248 is deployed as described above, for example, using the dual balloon technique, and attached within the iliac artery branch 18b. Next, another catheter, carrying limb 242 is positioned within the iliac artery branch 18a and positioned to release and expand stent 244 so as to engage shoulder 238 within the branch central space 232. Limb 242 is then further deployed from the catheter and attached within the iliac artery 18a using stent 246.

Figure 12:
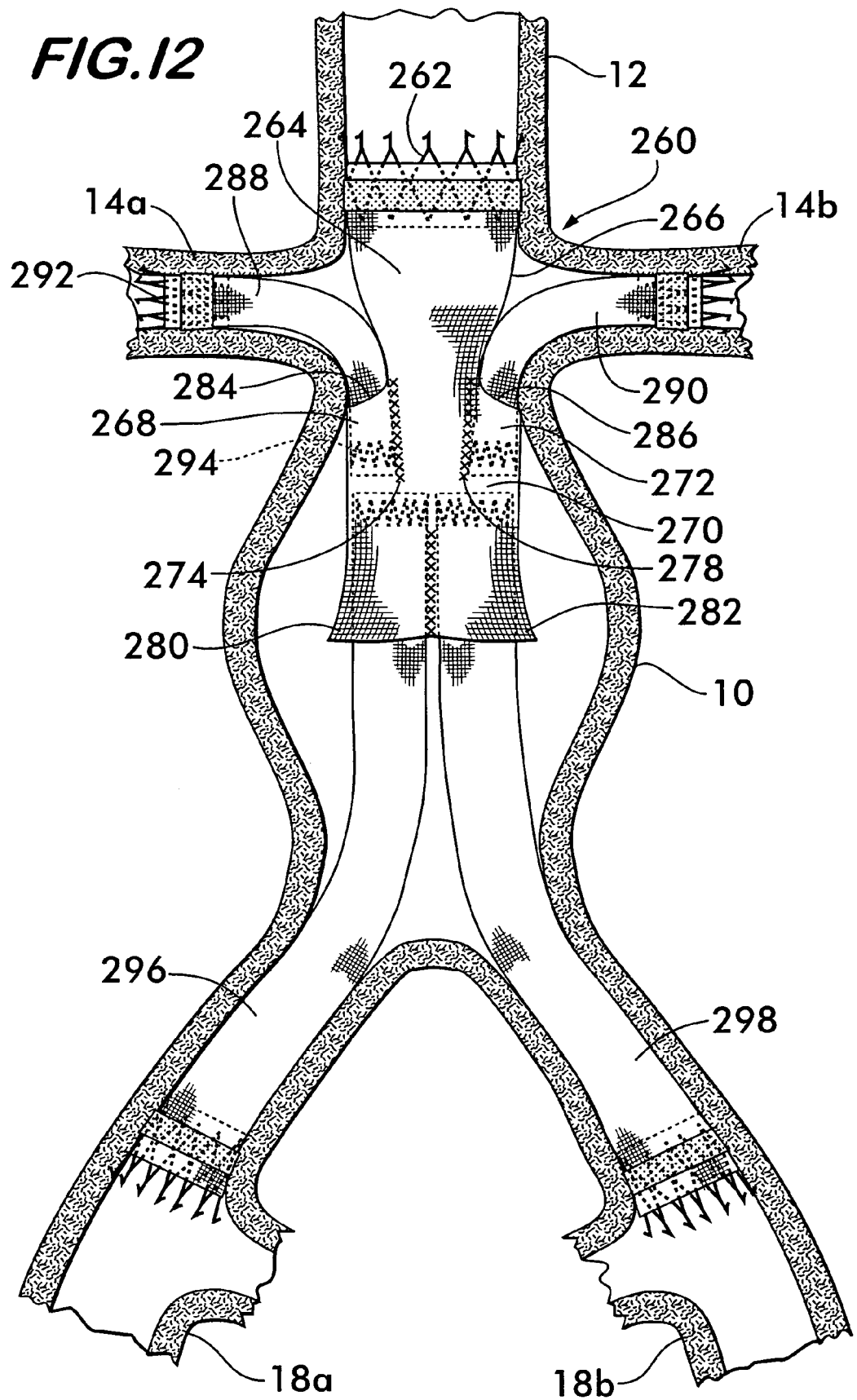
FIG. 12 is a longitudinal sectional view of yet another embodiment of an integral support stent graft assembly according to the invention.

Another embodiment 260 of the integral support stent graft assembly is shown in FIG. 12. Embodiment 260 is useful to repair aneurysm 10 in abdominal artery 12 where there is no healthy tissue region between the renal arteries 14a and 14b and the aneurysm 10 to which the stent graft assembly may be attached. In stent graft assembly 260, a stent 262 attaches a base module 264 to healthy tissue above the renal arteries 14a and 14b. The base module 264 comprises a perimetral sidewall 266 and is subdivided into three compartments, 268, 270 and 272. The division is made using lines of attachment 274 and 278 joining opposing portions of the perimetral sidewall 266 together. The base module 264 is further subdivided into branch sidewall portions 280 and 282 for receiving limbs as described above.

All three compartments 268, 270 and 272 are in fluid communication with the branch sidewall portions 280 and 282, but the outermost positioned compartments 268 and 272 are also in fluid communication with openings 284 and 286 in the perimetral sidewall 266. Openings 284 and 286 are positioned on opposite sides of the base module 264 and are adapted to receive tubes 288 and 290 providing fluid communication between the base module 264 and the renal arteries 14a and 14b respectively. Blood will flow to the kidneys from the abdominal aorta 12 through the renal arteries 14a and 14b in a retrograde flow regime through the tubes 288 and 290 in view of the fact that their proximal ends attached to the base module 264 point downwardly.

Embodiment 260 may be implanted via catheter techniques through the iliac arteries 18a or 18b as described above. Once the base module 264 is attached above the renal arteries 14a and 14b a guide wire is used to guide a catheter holding one of the tubes 288 through compartment 268 and into a renal artery 14a. The tube 288 is released from the catheter and attached within the renal artery, for example using a stent 292. The stent 292 may be self expanding or expandable by a balloon to engage the renal artery 14a and fix the tube 288 to it. The tube 288 is deployed from the catheter as the catheter is withdrawn, and a second stent 294 is used to engage the perimeter sidewall 266 forming compartment 268 (including the line of attachment 274) to fix the proximal end of tube 288 within the opening 284. The technique is repeated to join the other tube 290 to the renal artery 14b. Limbs 296 and 298 are subsequently attached between the base module 264 and the iliac arteries 18a and 18b as described above.

Figure 13:
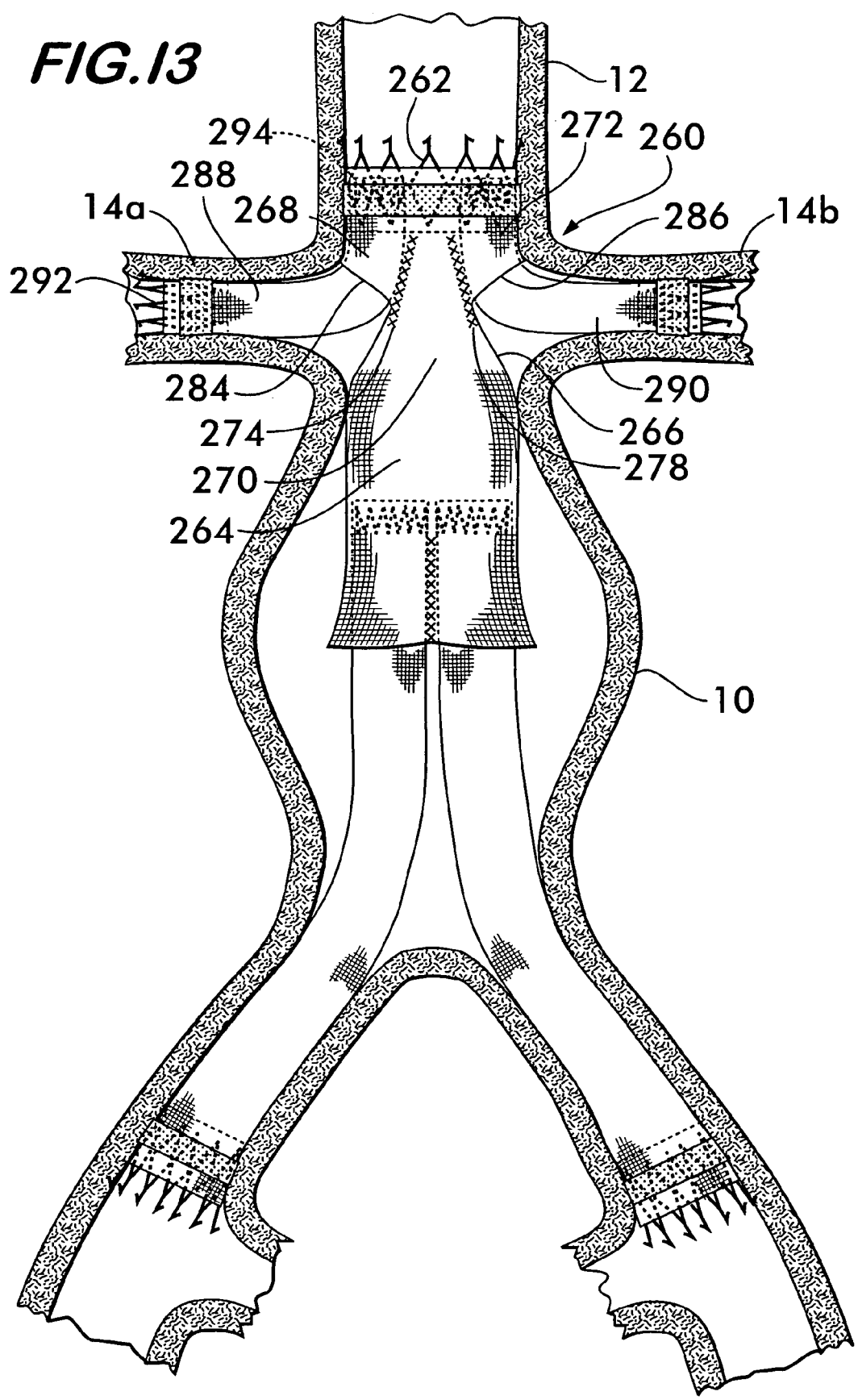
FIG. 13 is a longitudinal sectional view of still another embodiment of an integral support stent graft assembly according to the invention.

In FIG. 13, the tubes 288 and 290 are shown with proximal ends attached to the base module 264 facing upwardly into the aorta 12 to receive the flow of blood directly, as opposed to the retrograde flow as occurs in the embodiment shown in FIG. 12, wherein the proximal ends point downwardly. When the tubes 288 and 290 receive the direct flow they must be implanted using catheters which traverse the descending aorta as opposed to the iliac arteries.

Figure 14:
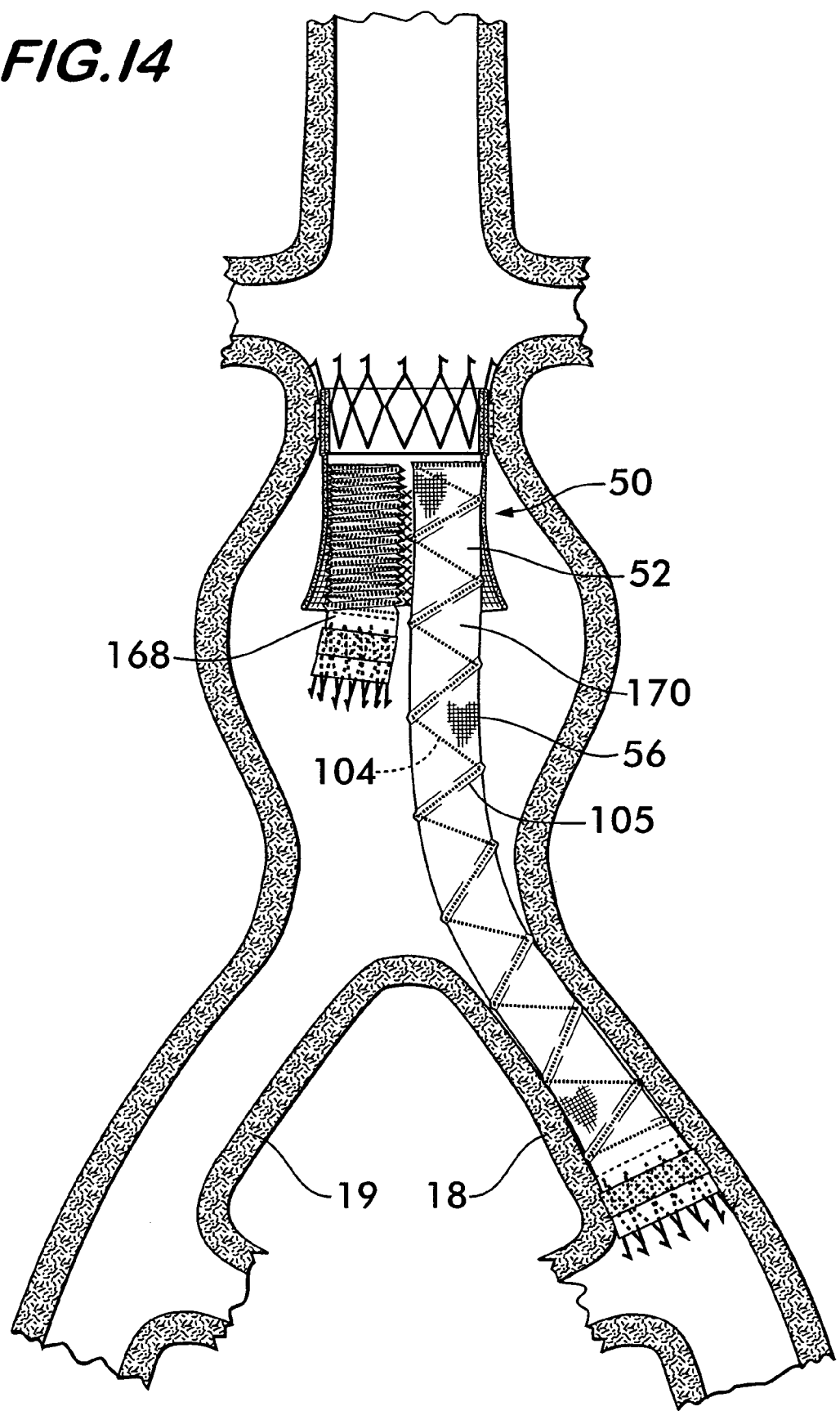
FIG. 14 is a longitudinal sectional view of again another embodiment of an integral support stent graft according to the invention.

Another embodiment, shown in FIG. 14, is a "unibody" device wherein the limbs 168 and 170 are integrally formed with the base module 52. This embodiment takes advantage of the lengthwise compressibility/compaction of the interweave comprising flexible filamentary members 56 and stiffening monofilaments 104 forming the limbs 168 and 170 to facilitate implantation. The limbs are compressed within the base module 52 as shown for limb 168, and drawn out into the iliac arteries as shown for limb 170 when implanted in the artery to repair the aneurysm.

Integral support stent graft assemblies according to the invention will provide distinct advantages over prior art stent grafts. For the modular embodiments, the assembly can be formed from components chosen on the basis of size to tailor the assembly to the needs of a particular patient. The ability to assemble the stent graft from components means that more size permutations may be accommodated with fewer stock parts than a single piece stent graft, wherein a different stent graft must be in stock or custom created for a range of each size variable. The base module is short, allowing precise placement on a target tissue region between arterial branches, for example, between the renal arteries and an aneurysm. The short size furthermore does not stiffen the catheter, facilitating its traversal through the artery. This is unlike prior art stent grafts wherein the entire stent graft is present in the catheter, causing significant increase in catheter stiffness.

By providing radial stiffness to the graft through corrugations formed by interwoven stiffening monofilaments, the grafts are adaptable to accommodate variations in size which occur over time or due to patient movement. Tapering the ends of the limbs These advantages should increase the success rate of aneurysm treatment while reducing the cost and trauma to the patient.

What is claimed is:

1. A stent graft for repair of a vascular vessel, said stent graft comprising:

a graft formed of a plurality of flexible filamentary members interwoven to form an elongated bifurcated tube having a first tube segment and two branch tube segments in fluid communication with said first tube segment at a bifurcation point, one of said branch tube segments being separable from said first tube segment, said first tube segment comprising a first sidewall portion defining a first central space and second and third sidewall portions defining second and third central spaces in fluid communication with said first central space, a line of attachment being formed between said second and third central spaces by joining opposing portions of said sidewall portions together, said line of attachment having a terminal point positioned at a junction of said first, second and third central spaces and thereby forming a shoulder within said graft, an end of said one branch segment having a first stent attached thereto and being insertable within one of said second and third central spaces, said end having said first stent being engageable with said shoulder, engagement between said end and said shoulder retaining said one branch segment to said first tube segment;

a stiffening monofilament interwoven with said flexible filamentary members, said monofilament extending helically around said tube and defining a plurality of circumferential corrugations in said tube; and a second stent positioned at one end of said tube, said second stent surrounding said end and being deformable between a collapsed configuration and an expanded configuration supporting said tube in an open configuration, said one end being tapered from a smaller to a larger diameter for providing sealing engagement with said vascular vessel.

2. A stent graft according to claim 1, wherein said flexible filamentary members are formed of a polymer and said stiffening monofilament is formed from a metal.

3. A stent graft according to claim 1, wherein said sidewall portions are joined by interweaving one to another along said line of attachment.

4. A stent graft according to claim 1, wherein:
said second stent comprises a plurality of first projections extending in a first direction and a plurality of second projections extending in a second direction opposite to said first projections; and
said one end of said tube comprises a reverse fold having a plurality of first openings in said tube in a first row extending circumferentially around said reverse fold, and a plurality of second openings in said tube in a second row extending circumferentially around said reverse fold, said first and second rows being positioned in spaced relation to one another, said second stent being positioned between said first and second rows, said first projections extending through said first openings in said first row and said second projections extending in an opposite direction through said second openings in said second row, said second stent being thereby retained to said graft.

5. A stent graft according to claim 4, wherein said first and second projections comprise a plurality of interconnected loops that extend circumferentially to form a ring surrounding said one end of said tube.

6. A stent graft according to claim 4, wherein said reverse fold and a portion of said tube adjacent to said first fold are comprised of a sidewall of said tube having a reduced thickness in comparison with the remainder of said tube.

7. A stent graft according to claim 6, wherein said reverse fold and said portion of said tube adjacent to said first fold each have a thickness of ½ of the thickness of the remainder of said tube.

8. A stent graft according to claim 4, further comprising a region of enhanced biocompatibility positioned on said tube adjacent to said reverse fold, said region of enhanced biocompatibility facing radially outwardly and facilitating the formation of a biological seal between said stent graft and said vascular vessel.

9. A stent graft according to claim 8, wherein said region of enhanced biocompatibility comprises interstices formed in said tube to facilitate ingrowth of living tissue forming said vascular vessel.

10. A stent graft according to claim 8, wherein said region of enhanced biocompatibility comprises interweaving filaments into said tube that provoke a healing reaction in living tissue.

11. A stent graft according to claim 8, wherein said region of enhanced biocompatibility comprises coating said tube adjacent to said reverse fold with compounds that provide a healing reaction in living tissue.

12. A stent graft for repair of a vascular vessel, said stent graft comprising:

a first tube segment including a first sidewall portion defining a first central space and second and third sidewall portions defining second and third central spaces in fluid communication with said first central space, a line of attachment being formed between said second and third central spaces by joining opposing portions of said sidewall portions together, said line of attachment having a terminal point positioned at a junction of said first, second and third central spaces and thereby forming a shoulder within said graft; and a first branch segment having a stent positioned at one end thereof, said one end being inserted within said second central space and engaged with said shoulder, engagement between said first branch segment and said shoulder retaining said first branch segment to said first tube segment.

13. A stent graft according to claim 12, further comprising a second branch segment having a second stent positioned at one end thereof, said one end of said second branch segment being insertable within said third central space and being engageable with said shoulder, engagement between said second branch segment and said shoulder retaining said second branch segment to said first tube segment.

14. A stent graft according to claim 12, wherein said first branch segment has a second stent positioned at an opposite end thereof, said second stent surrounding said opposite end, said opposite end being tapered from a smaller to a larger diameter for providing sealing engagement with said vascular vessel.

15. A stent graft according to claim 12, wherein said first tube segment is formed of a plurality of interwoven flexible filamentary members and a stiffening monofilament interwoven with said flexible filamentary members, said monofilament extending helically around said first tube segment and forming a reinforcing rib integral with said first tube segment thereby defining a plurality of circumferential corrugations in said tube.

16. A stent graft for repair of a vascular vessel, said stent graft comprising:

a stent having a plurality of first projections extending in a first direction and a plurality of second projections extending in a second direction opposite to said first projections; and a graft formed of a plurality of flexible filamentary members interwoven to form an elongated tube, one end of said tube comprising a reverse fold having a plurality of first openings in said tube in a first row extending circumferentially around said reverse fold, and a plurality of second openings in said tube in a second row extending circumferentially around said reverse fold, said first and second rows being positioned in spaced relation to one another, said stent being positioned between said first and second rows, said first projections extending through said first openings in said first row and said second projections extending in an opposite direction through said second openings in said second row, said stent being thereby retained to said graft.

* * * * *